United States Patent
Jackson

(10) Patent No.: US 7,204,838 B2
(45) Date of Patent: Apr. 17, 2007

(54) MEDICAL IMPLANT FASTENER WITH NESTED SET SCREW AND METHOD

(76) Inventor: Roger P. Jackson, 4706 W. 86th St., Prairie Village, KS (US) 66207

(*) Notice: Subject to any disclaimer, the term of this patent is extended or adjusted under 35 U.S.C. 154(b) by 199 days.

(21) Appl. No.: 11/024,543

(22) Filed: Dec. 20, 2004

(65) Prior Publication Data

US 2006/0149235 A1    Jul. 6, 2006

(51) Int. Cl.
*A61B 17/56* (2006.01)

(52) U.S. Cl. .................................................. 606/61

(58) Field of Classification Search .................. 606/61, 606/72, 73
See application file for complete search history.

(56) References Cited

U.S. PATENT DOCUMENTS

| | | |
|---|---|---|
| 2,243,717 A | 5/1941 | Moreira |
| 3,236,275 A | 2/1966 | Smith |
| 3,604,487 A | 9/1971 | Gilbert |
| 3,640,416 A | 2/1972 | Temple |
| 4,041,939 A | 8/1977 | Hall |
| 4,373,754 A | 2/1983 | Bollfrass et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,887,596 A | 12/1989 | Sherman |
| 4,950,269 A | 8/1990 | Gaines, Jr. |
| 5,005,562 A | 4/1991 | Cotrel |
| 5,022,791 A | 6/1991 | Isler |
| 5,034,011 A | 7/1991 | Howland |
| 5,037,259 A * | 8/1991 | Duran et al. ................ 411/173 |

(Continued)

FOREIGN PATENT DOCUMENTS

DE    4425392    11/1995

(Continued)

OTHER PUBLICATIONS

*Spine*, Lipcott, Williams & Wilkins, Inc. vol. 24, No. 15, p. 1495.

(Continued)

*Primary Examiner*—Eduardo C. Robert
*Assistant Examiner*—Michael J. Araj
(74) *Attorney, Agent, or Firm*—John C. McMahon

(57) ABSTRACT

A nested fastener and set screw combination for securing a spinal fixation rod to a bone screw includes a fastener base receivable into an open channel of a bone screw. The fastener base has a central threaded bore to receive a threaded set screw. The set screw is provided with projecting structure, such as a ring, point or dome-shaped structure, for positive engagement with the surface of a rod. Uploaded and downloaded set screw embodiments are disclosed. In an uploaded set screw embodiment, the fastener base is provided with a radially inwardly extending abutment shoulder to engage and abut the set screw, prohibiting advancement of the set screw out of a top of the fastener and allowing for simultaneous removal of the set screw and the fastener. In an embodiment, the fastener includes a break-off head that separates from the fastener when a pre-selected installation torque is exceeded.

35 Claims, 7 Drawing Sheets

U.S. PATENT DOCUMENTS

| | | | |
|---|---|---|---|
| 5,067,955 A | 11/1991 | Cotrel | |
| 5,092,635 A | 3/1992 | DeLange et al. | |
| 5,102,412 A | 4/1992 | Rogozinski | |
| 5,129,388 A | 7/1992 | Vignaud et al. | |
| 5,147,363 A | 9/1992 | Harle | |
| 5,154,719 A | 10/1992 | Cotrel | |
| 5,176,483 A | 1/1993 | Baumann et al. | |
| 5,217,497 A | 6/1993 | Mehdian | |
| 5,257,993 A | 11/1993 | Asher et al. | |
| 5,261,907 A | 11/1993 | Vignaud et al. | |
| 5,261,912 A | 11/1993 | Frigg | |
| 5,275,601 A | 1/1994 | Gogolewski et al. | |
| 5,306,275 A | 4/1994 | Bryan | |
| 5,321,901 A | 6/1994 | Kelly | |
| 5,346,493 A | 9/1994 | Stahurski et al. | |
| 5,358,289 A | 10/1994 | Banker et al. | |
| 5,385,583 A | 1/1995 | Cotrel | |
| 5,427,418 A | 6/1995 | Watts | |
| 5,443,467 A | 8/1995 | Biedermann | |
| 5,468,241 A | 11/1995 | Metz-Stavenhagen et al. | |
| 5,474,555 A | 12/1995 | Puno et al. | |
| 5,487,742 A | 1/1996 | Cotrel | |
| 5,490,750 A | 2/1996 | Gundy | |
| 5,496,321 A | 3/1996 | Puno | |
| 5,499,892 A * | 3/1996 | Reed | 411/5 |
| 5,507,745 A | 4/1996 | Logroscino et al. | |
| 5,545,165 A | 8/1996 | Biedermann et al. | |
| 5,562,663 A | 10/1996 | Wisnewski et al. | |
| 5,569,251 A | 10/1996 | Baker et al. | |
| 5,601,553 A | 2/1997 | Trebing et al. | |
| 5,607,304 A | 3/1997 | Bailey et al. | |
| 5,607,425 A | 3/1997 | Rogozinski | |
| 5,607,428 A | 3/1997 | Lin | |
| 5,611,800 A | 3/1997 | Davis et al. | |
| 5,628,740 A | 5/1997 | Mullane | |
| 5,630,817 A | 5/1997 | Rokegem | |
| 5,641,256 A | 6/1997 | Gundy | |
| 5,643,260 A | 7/1997 | Doherty | |
| 5,643,261 A | 7/1997 | Schafer et al. | |
| 5,662,652 A | 9/1997 | Schafer et al. | |
| 5,662,653 A | 9/1997 | Songer et al. | |
| 5,669,909 A | 9/1997 | Zdeblick et al. | |
| 5,672,176 A | 9/1997 | Biedermann et al. | |
| 5,683,390 A | 11/1997 | Metz-Stavenhagen et al. | |
| 5,697,929 A | 12/1997 | Mellinger | |
| 5,711,709 A | 1/1998 | McCoy | |
| 5,713,898 A | 2/1998 | Stucker et al. | |
| 5,723,013 A | 3/1998 | Jeanson et al. | |
| 5,725,527 A | 3/1998 | Biedermann et al. | |
| 5,728,098 A | 3/1998 | Sherman et al. | |
| 5,733,286 A | 3/1998 | Errico et al. | |
| 5,738,685 A | 4/1998 | Halm et al. | |
| 5,741,254 A | 4/1998 | Henry et al. | |
| 5,752,957 A | 5/1998 | Ralph et al. | |
| 5,782,833 A | 7/1998 | Haider | |
| 5,797,911 A | 8/1998 | Sherman et al. | |
| 5,800,547 A | 9/1998 | Schafer et al. | |
| 5,944,465 A | 8/1999 | Janitzki | |
| 5,964,767 A * | 10/1999 | Tapia et al. | 606/73 |
| 6,001,098 A | 12/1999 | Metz-Stavenhagen et al. | |
| 6,004,349 A | 12/1999 | Jackson | |
| 6,059,786 A | 5/2000 | Jackson | |
| 6,063,090 A | 5/2000 | Schlapfer | |
| 6,086,614 A * | 7/2000 | Mumme | 623/18.11 |
| 6,102,913 A | 8/2000 | Jackson | |
| 6,117,137 A | 9/2000 | Halm et al. | |
| 6,143,032 A | 11/2000 | Schafer et al. | |
| 6,224,598 B1 | 5/2001 | Jackson | |
| 6,231,575 B1 * | 5/2001 | Krag | 606/61 |
| 6,235,034 B1 | 5/2001 | Bray | |
| 6,254,146 B1 | 7/2001 | Church | |
| 6,296,642 B1 | 10/2001 | Morrison et al. | |
| 6,315,564 B1 | 11/2001 | Levisman | |
| 6,402,757 B1 | 6/2002 | Moore et al. | |
| 6,485,492 B1 | 11/2002 | Halm et al. | |
| 6,540,749 B2 | 4/2003 | Schafer et al. | |
| 6,551,323 B2 | 4/2003 | Doubler et al. | |
| 6,669,422 B1 * | 12/2003 | Sterle | 411/384 |

FOREIGN PATENT DOCUMENTS

| | | |
|---|---|---|
| DE | 19509331 | 9/1996 |
| DE | 29806563 | 7/1998 |
| DE | 29810798 | 12/1999 |
| DE | 19951145 | 5/2001 |
| EP | 0885598 | 12/1998 |
| WO | WO 92/03100 | 3/1992 |
| WO | WO 94/10927 | 5/1994 |
| WO | WO 94/26191 | 11/1994 |

OTHER PUBLICATIONS

Brochure of Tyco/Healthcare/Surgical Dynamics on Spiral Radius 90D, Publication Date: Sep. 2001, pp. 1-8.

* cited by examiner

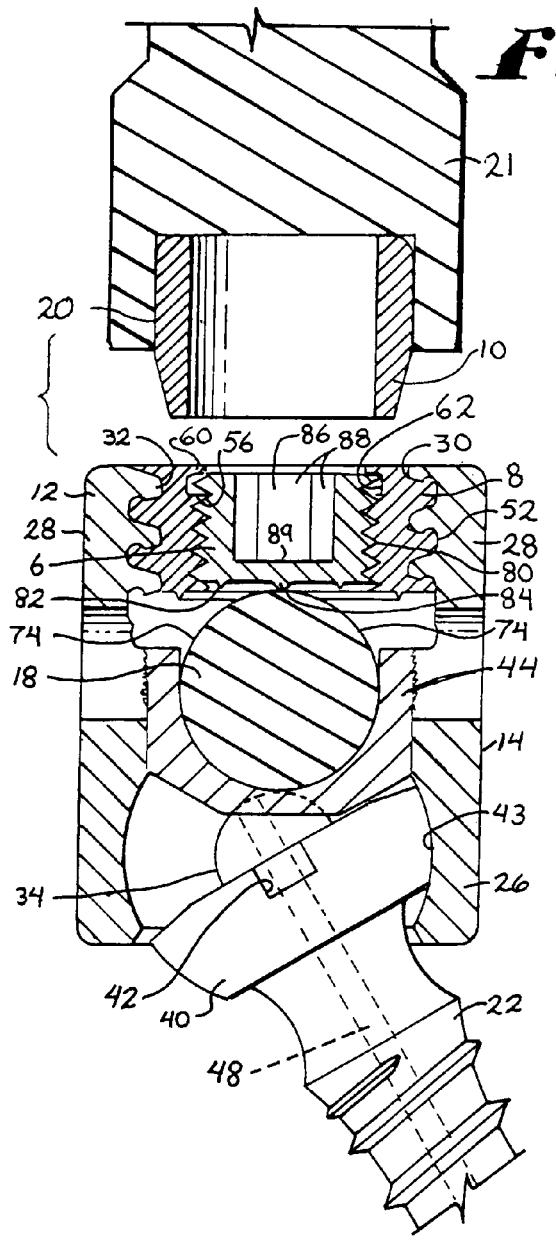
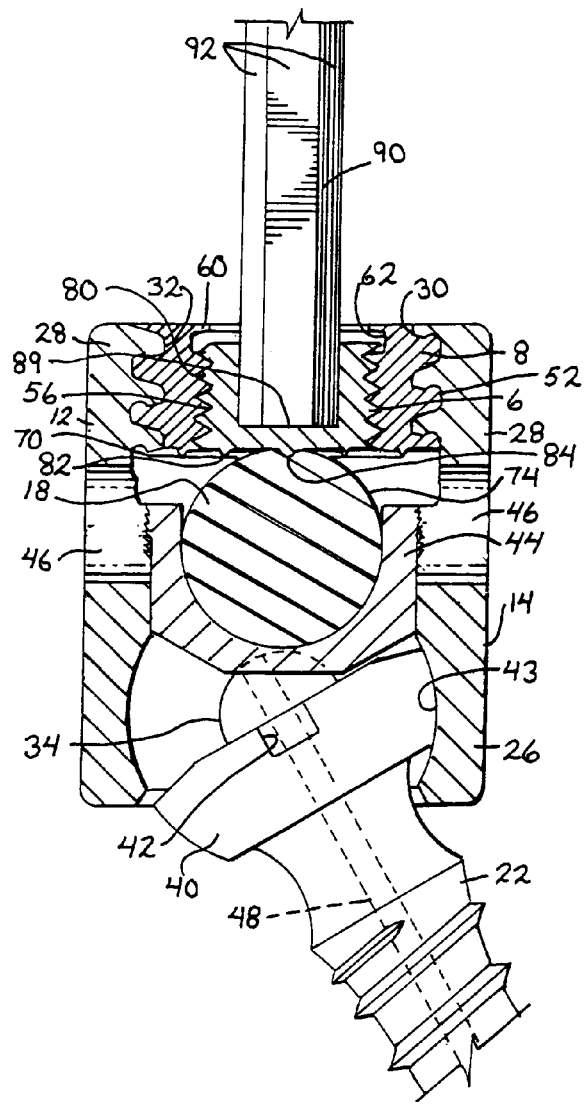

US 7,204,838 B2

MEDICAL IMPLANT FASTENER WITH NESTED SET SCREW AND METHOD

BACKGROUND OF THE INVENTION

The present invention is directed to a closure mechanism or fastener for medical implants and more specifically, to a coaxially nested fastener with an up- or down-loaded central set screw.

Bone screws are utilized in many types of spinal surgery, such as for osteosynthesis, in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged onto an open receiver channel of such a head.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A rod is positioned in the U-shaped channel in generally perpendicular relation to the shank and the open end of the yoke is closed off by a closure device. The closure device is tightened against the rod to clamp the rod in place against the bottom of the channel. The closure device must positively secure the rod in place to prevent rotational or translational movement of the rod relative to the bone screw and the bone in which it is anchored. Conventional types of closure devices include a threaded fastener which is screwed into threads formed into the surfaces forming the U-shaped channel or a nut with an inner thread that mates with threads disposed on outer surfaces of the arms.

Fasteners disposed within the arms of a bone screw head are often preferable to nuts as such fasteners take up less space. In order to perform adequately, such a fastener is tightly torqued relative to the bone screw to secure the bone screw to the rod and prevent relative rotation or translation. When the rod is straight, this is readily accomplished. However, in typical spinal fixation applications, the rod is almost always bent at the location of each bone screw to correctly position the rod for normal or desired curvature of the spinal column. Because the rod is bent, it does not flatly engage the bottom of the groove or U-shaped channel in the head of the bone screw, but tends to be raised from the bottom of the channel at one or both ends. Thus, when a conventional fastener is installed, an outer periphery of the lower end of the fastener most likely engages parts of the rod that are not set snugly against the floor that forms the bone screw channel. After installation, when the patient's back is bent during movement activities, the rod may flex slightly relative to the bone screw. Over time, such flexure may allow the rod to move, either translationally or rotationally, causing the fastener to work loose. Consequently, it is desirable to develop fasteners particularly configured for secure engagement to a spinal implant rod that resist forces placed upon the fastener that tend to loosen the fastener from the bone screw head due to rod flexure caused by patient movement.

SUMMARY OF THE INVENTION

A nested fastener and set screw combination for securing a structural element, such as a rod, within a receiver of a medical implant, such as a open-headed bone screw, includes an outer fastener or plug portion adapted to be interferingly positioned within the opening of the receiver so as to close the opening when in an installed configuration. The fastener has a through bore extending from a first end to a second end thereof. The bore is defined at least in part by an inner guide and advancement structure, such as a V-thread, but may be of a variety of helical guide and advancement structures. A set screw has an outer, complimentary guide and advancement structure rotatingly mateable with the inner guide and advancement structure of the fastener. The set screw is loadable and receivable in the bore of the fastener and includes a tool engagement formation adapted for non-slip engagement of the set screw by a set screw installment and removal tool. Up- and down-loadable set screw embodiments are provided. The set screw has a setting configuration wherein the set screw is in engagement with the structural element or rod.

In one embodiment, an abutment shoulder interferingly prohibits advancement of the set screw out of the second end of the fastener. Such an abutment shoulder may be an annular projection extending from the fastener inwardly into the bore and disposed near an upper end of the fastener. The abutment shoulder allows for removal of the fastener and the set screw as a single unit utilizing the set screw installment and removal tool.

Both the fastener and the set screw may include interference structure projecting therefrom. Such interference structure are shaped and positioned to operably cut into a surface of the structural element in the setting configuration. For example, the interference structure may be in the form of a pointed projection or ring.

In a particular embodiment, the interference structure is a curved, dome-like or partially spherical or hemispherical structure projecting from a base of the set screw along a central axis thereof. The interference structure provides compressive force along a central axis of the set screw when in a setting configuration wherein the interference structure is in frictional engagement with the structural element or rod.

A method of the invention includes up-loading a set screw into a fastener having an abutment shoulder by inserting the set screw into a bottom of the fastener and rotating the set screw with respect to the fastener until the set screw abuts the abutment shoulder. In a subsequent step, the nested fastener and set screw are inserted in a medical implant receiver opening, with the fastener being rotated until a break-off head breaks from the fastener at a preselected torque. The nested set screw is then driven by rotation into engagement with a rod or other structural element.

OBJECT AND ADVANTAGES OF THE INVENTION

Therefore, objects of the present invention include: providing an improved spinal implant assembly for implantation into vertebrae of a patient; providing such an assembly that includes an open-headed implant, a rod or other structural element and an implant fastener that secures the rod to the implant; providing such an assembly that includes an inner set screw retainable in the implant fastener; providing such an assembly that has a low profile after final installation; providing such an assembly in which the set screw is provided with a formation or formations to enable non-slip engagement of the set screw by an installation and removal tool; providing such an assembly in which the set screw is provided with interference structure for providing compressive force along a central axis of the set screw upon frictional engagement with a rod or other structural element; and providing such an assembly that is easy to use, especially adapted for the intended use thereof and wherein the implant assembly components are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is a reduced cross-sectional view similar to FIG. 4, showing the break-off head of the fastener being removed with a torquing tool.

FIG. 6 is a cross-sectional view similar to FIG. 5 shown with a set screw tool.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
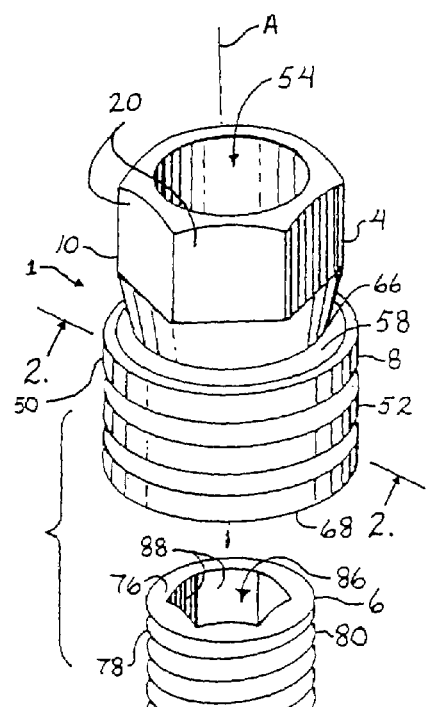
FIG. 1 is an exploded perspective view of an assembly according to the invention including a fastener having a break-off head and an inner set screw.
Figure 2:
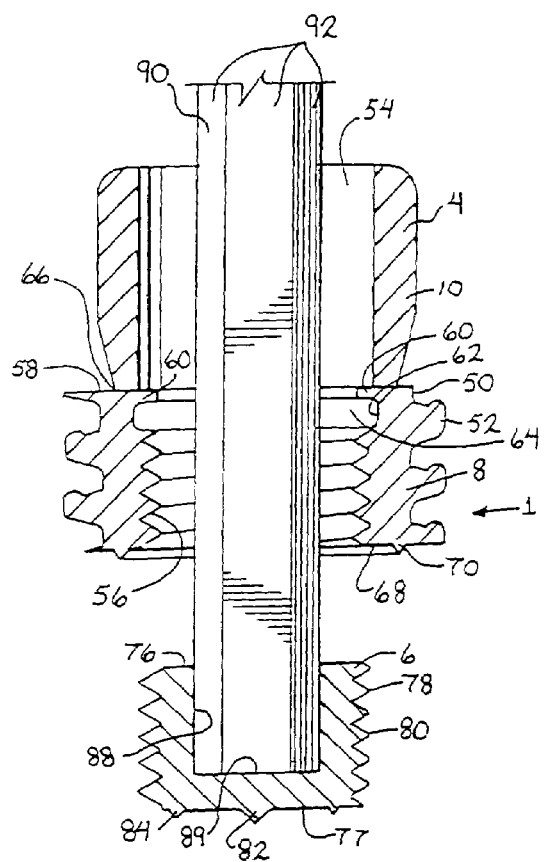
FIG. 2 is an enlarged cross-sectional view taken along the line 2—2 of FIG. 1 and shown with a set screw tool.
Figure 3:
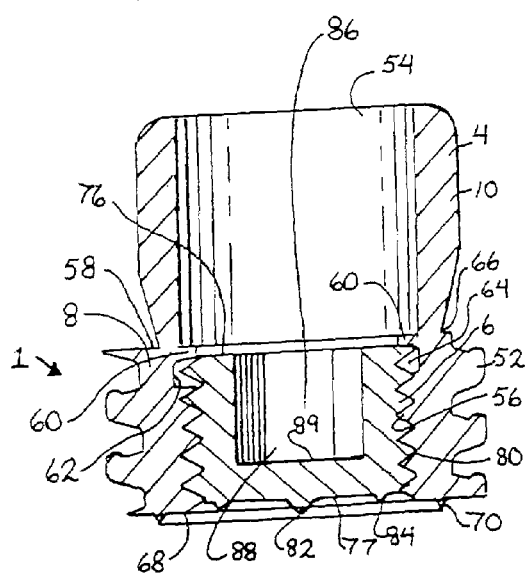
FIG. 3 is a cross-sectional view similar to FIG. 2, showing the set screw inserted in the fastener.

With reference to FIGS. 1–3, the reference numeral 1 generally designates a nested implant fastener assembly according to the present invention. The assembly 1 includes a fastener 4 and an uploaded set screw 6. The fastener 4 includes a base 8 integral or otherwise attached to a break-off head 10. The base 8 cooperates with a head 12 of a bone screw 14, as illustrated in FIGS. 4–7, to close an open channel 16 formed by the head 12 and to clamp a spinal fixation rod 18 within the bone screw head 12. The break-off installation head 10 includes a faceted outer surface 20 sized and shaped for engagement with a tool 21 for installing the fastener 4 to the bone screw 14 and thereafter separating the break-off head 10 from a respective base 8 when installation torque exceeds selected levels.

As illustrated in FIGS. 4–7, one kind of bone screw 14 for use with the fastener assembly 1 includes a threaded shank 22 for implanting or anchoring in a bone such as a vertebra 24. The threaded shank 22 of the bone screw 14 is pivotally attached to the substantially cylindrically shaped head 12 that includes a base 26 and spaced arms 28 that define the open U-shaped channel 16 for receiving the rod 18 or other elongate spinal fixation structure. The rod receiving channel 16 is sized so that the rod 18 fits snugly therein to maximize clamping or frictional engagement of the rod 18 with surfaces forming the channel 16.

Each of the arms 28 has an interior surface 30 that defines an inner substantially cylindrical profile and includes a partial, helically wound guide and advancement structure 32. In the illustrated embodiment, the guide and advancement structure 32 is a partial helically wound flangeform configured to mate under rotation with a similar structure on the fastener 4, as described more fully below. However, it is foreseen that the guide and advancement structure 32 could alternatively be a V-shaped thread, a buttress thread, a reverse angle thread or other thread-like or non-thread-like helically wound advancement structure for operably guiding under rotation and advancing the implant fastener 4 downward between the spaced arms 28. It is noted that any reference to the words top, bottom, up and down, and the like, in this application refers to the alignment shown in the various drawings, as well as the normal connotations applied to such devices, and is not intended to restrict positioning of the assembly 1 in actual use.

In the illustrated embodiment, the bone screw shank 22 further includes an upper capture portion 34 integral with the threaded shank 22. The capture portion 34 includes a threaded projection 36 having a domed top 38. A retainer structure or ring 40 is threadably attached to the threaded projection 36, retaining the upper capture portion 34 within the base 26 of the bone screw head 12. The ring 40 includes an open through-slot 42 sized and shaped to receive an installation tool (not shown) for driving the threaded shank 22 into the vertebra 24.

An inner surface 43 of the head 12 and the retainer ring 40 that is attached to the upper shank portion 34 cooperate in such a manner that the head 12 and shank 22 can be secured at any of a plurality of angles, articulations or rotational alignments relative to one another and within a selected range of angles both from side to side and from front to rear, to enable flexible or articulated engagement of the head 12 with the shank 22 until both are locked or fixed relative to each other near the end of an implantation procedure. The inner surface 43 is preferably hemispherical, but may be of another shape, such as conical. The top 38 is preferably convex, curved or dome-shaped as shown in the drawings, for possible positive engagement with the rod 18 in any alignment of the shank 22 relative to the head 14.

In the illustrated embodiment shown in FIGS. 4–7, the domed top 38 does not come into direct contact with the rod 18, but rather a side-loading insert 44 is received within the bone screw head 12 prior to rod insertion, and ultimately is positioned between the rod 18 and the top 38. The insert 44 is ratcheted downwardly into contact with the domed top 38, functioning to set the articulation of the shank 22 with respect to the bone screw 14 prior to final locking of the rod 18 into the head 12. Side apertures 46 formed in the head 12 allow for manipulation and release of the insert 44 with respect to pressure on the dome shaped top 38. It is foreseen that a top loaded insert may also be utilized with the assembly 1 of the invention, or alternatively, the bone screw head and shank may be structured such that no insert is used so that the dome top 38 directly engages the rod.

In the illustrated embodiment, the shank 22 is cannulated, having a small central bore 48 extending an entire length of the shank 22. The bore 48 is coaxial with the threaded shank 22 and provides a passage through the shank 22 interior for a pin or length of wire (not shown) inserted into the vertebra 24 prior to the insertion of the shank 22, the wire providing a guide for insertion of the shank 22 into the vertebra 24.

It is noted that the nested implant fastener assembly 1 of the present invention can be used with virtually any type of open-ended bone screw, including fixed monoaxial and polyaxial bone screws of many different types wherein the head is locked relative to the shank by structure other than in the manner described in the illustrated embodiment.

The base 8 of the fastener 4 is substantially cylindrical, having an axis of rotation A and an external surface 50 having a guide and advancement structure 52 disposed thereon. The guide and advancement structure 52 is matingly attachable to the guide and advancement structure 32 of the bone screw head 12. As with the guide and advancement structure 32, the guide and advancement structure 52 can be of any type, including V-type threads, buttress threads, reverse angle threads, or square threads. Preferably the guide and advancement structure 52 is a helically wound flange form that interlocks with the reciprocal flange form as part of the guide and advancement structure 32 on the interior of the bone screw arms 28. The guide and advancement structures 32 and 52 are preferably of a type that do not exert radially outward forces on the arms 28 and thereby avoid tendencies toward splaying of the arms 28 of the bone screw head 12, when the fastener 4 is tightly torqued into the head 12.

The fastener 4 includes an internal, centrally located through-bore 54. At the base 8, the bore 54 is substantially defined by a guide and advancement structure, shown in FIGS. 1–7 as an internal V-shaped thread 56. The thread 56 is sized and shaped to receive the threaded set screw 6 therein as will be discussed in more detail below. Although a traditional V-shaped thread 56 is shown, it is foreseen that other types of helical guide and advancement structures may be used. Near a substantially annular planar top surface 58 of the base 8, an abutment shoulder 60, extends uniformly radially inwardly. The abutment shoulder 60 is spaced from the V-shaped thread 56 and sized and shaped to be a stop for the set screw 6, prohibiting the set screw 6 from advancing out of the top 58 of the base 8. It is foreseen that alternatively, the set screw 6 may be equipped with an outwardly extending abutment feature near a base thereof, with complimentary alterations made in the base 8, such that the set screw 6 would be prohibited from advancing out of the top 58 of the base 8 due to abutment of such outwardly extending feature against a surface of the base 8.

In the embodiment illustrated in FIGS. 1–3, an inner cylindrical wall 62 separates the abutment shoulder 60 from the thread 56. The cylindrical wall 62 has a diameter slightly greater than a root or major diameter of the internal thread 56. The wall 62 partially defines a cylindrical space or passage 64 for axial adjustable placement of the screw 6 with respect to the rod 18 as will be discussed in more detail below.

The fastener 4 further includes the break-off head 10 that is integral or otherwise attached to the fastener 4 at a neck or weakened region 66. The neck 66 is dimensioned in thickness to control the torque at which the break-off head 10 separates from the fastener 4. The preselected separation torque of the neck 66 is designed to provide secure clamping of the rod 18 by the fastener 4 before the head 10 separates. For example, 120 inch pounds of force may be a selected break-off torque. The illustrated, hexagonal faceted surfaces 20 of the break-off head 10 enables positive, non-slip engagement of the head 10 by the installation and torquing tool 21 illustrated in FIG. 5. Separation of the break-off head 10 leaves only the more compact base 8 of the fastener 4 installed in the bone screw head 12, so that the installed fastener 4 has a low profile.

The base 8 of the fastener 4 may include structure to provide clamping engagement between the base 8 and the rod 18. In the embodiment disclosed in FIGS. 1–7, a bottom surface 68 of the base 8 has an interference structure in the form of a "cup point" or V-shaped ridge or ring 70. The V-ring 70 operably cuts into a surface 74 of the rod 18 during assembly, when the fastener 4 is threaded into the screw head 12, so that the fastener more positively secures the rod 18 against rotational and translational movement of the rod 18 relative to the head 12 of the bone screw 14. As the rod 18 may be bent or skewed with respect to the head 12 at a location of engagement between the rod 18 and the fastener 4, only a portion or a side of the V-ring 70 may engage with and cut into the rod 18. It is also foreseen that in some embodiments, clamp enhancing structure disposed on the fastener 4 may not be necessary or desirable.

The uploadable set screw 6 has a substantially planar top 76 and a bottom 77. The screw 6 is substantially cylindrical in shape, having an axis of rotation B, and includes an outer cylindrical surface 78 with a V-shaped thread 80 extending from the top 76 to the bottom 77 thereof. The surface 78 and thread 80 are sized and shaped to be received by and mated with the inner thread 56 of the fastener base 8 in a nested relationship. Thus, in operation, the axis of rotation B is the same as the axis of rotation A of the fastener 4. The embodiment of the set screw 6 best illustrated in FIGS. 1–3 includes interference structure for enhancing clamping or setting engagement with the surface 74 of the rod 18. The bottom 77 of the illustrated set screw 6 has a centrally located set point 82 and a peripherally located cup point or V-shaped set ring 84 projecting therefrom. The set point 82 and the set ring 84 are designed to cut into the surface 74 of the rod 18 when the set screw 6 is tightly fastened into the fastener base 8. The set point 82 projects outwardly from the bottom 77 to a location beyond the outermost surface of the set ring 84. Thus, the set point 82 is an initial and primary source of engagement with the rod 18, directly pressing against the rod 18 along the central axis of rotation B of the set screw 6. As with the V-ring 70 of the fastener 4, the V-ring 84 may contact and press against the rod 18 only along a portion thereof if the rod 18 is bent or otherwise disposed in a skewed relationship with the bone screw head 12. It is foreseen that other structures for enhancing clamping, such as knurling or the like may be used in some embodiments or none in others.

Figure 7:
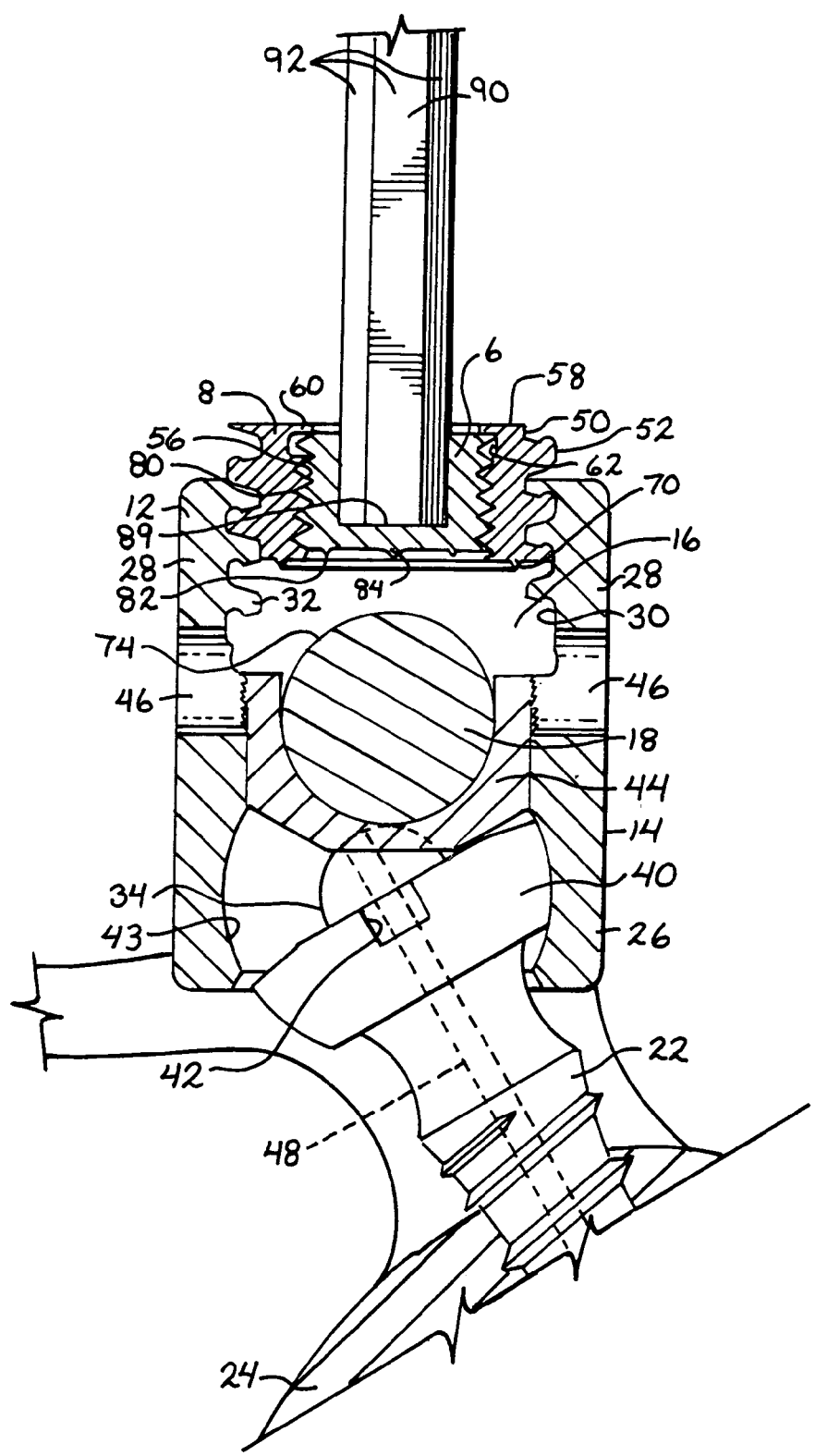
FIG. 7 is a cross-sectional view similar to FIG. 6 showing removal of the fastener and attached set screw with the set screw tool.
Figure 8:
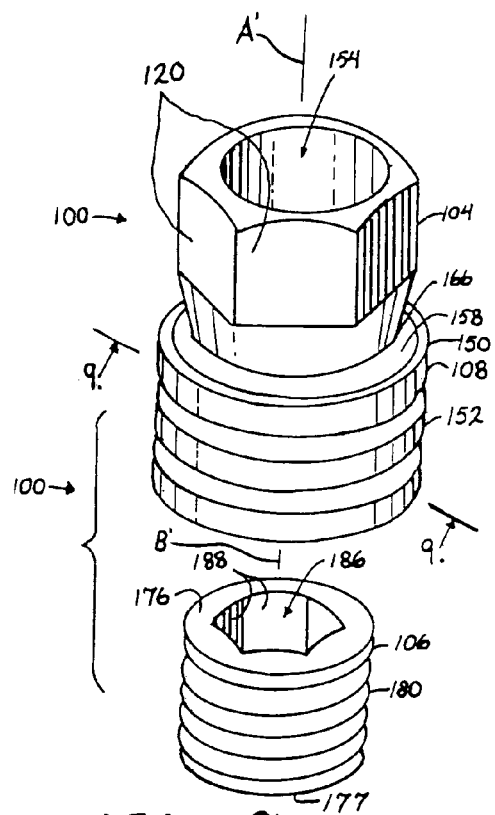
FIG. 8 is an exploded perspective view of a second embodiment of an assembly according to the invention including a fastener having a break-off head and an inner set screw.

The set screw 6 includes a central aperture 86 formed in the top 76 and defined by faceted side walls 88 and a hexagonal bottom seating surface 89, forming a hex-shaped internal drive for positive, non-slip engagement by a set screw installment and removal tool such as an Allen-type wrench 90 as depicted in FIGS. 2, 6 and 7. With reference to FIG. 2, the central aperture 86 cooperates with the central internal bore 54 of the fastener 4 for accessing and uploading the set screw 6 into the fastener 4 prior to engagement with the bone screw 14. After the assembly 1 engages the bone screw head 12, and the break-off head 10 is broken off, the tool 90 is used to set and lock the set screw 6 against the rod 18 as illustrated in FIGS. 6 and 7.

There are circumstances under which it is desirable or necessary to release the rod 18 from the bone screw 14. For example, it might be necessary for a surgeon to re-adjust components of a spinal fixation system, including the rod 18, during an implant procedure, following an injury to a person with such a system implanted. In such circumstances, the tool 90 may be used to remove both the set screw 6 and attached fastener base 8 as a single unit, with the set screw 6 contacting and contained within the base 8 by the abutment shoulder 60. Thus, rotation of the tool 90 engaged with the set screw 6 backs both the set screw 6 and the fastener base 8 out of the guide and advancement structure 32 in the arms 28 of the bone screw head 12, thereby releasing the rod 18 for removal from the bone screw 14 or repositioning of the rod 18. It is foreseen that other removal structures such as side slots or other screw receiving and engagement structures may be used to engage the set screw 6 that is nested in the fastener base 8.

In use, the set screw 6 is assembled with the fastener 4 prior to insertion in the bone screw head 12. With reference to FIG. 2, the Allen-type tool 90 is inserted through the bore 54 of the fastener 4 and into the aperture 86 of the set screw 6 until seated on the bottom surface 89, with faceted outer surfaces 92 of the tool 90 engaging the inner faceted walls 88 of the set screw 6. The set screw 6 is then uploaded into the fastener 4 by rotation of the set screw 6 with respect to the fastener 4 to mate the set screw thread 80 with the fastener inner thread 56 until the set screw top surface 76 abuts the abutment shoulder 60, resulting in the nested arrangement of the assembly 1 shown in FIG. 3, with the set screw 6 completely enveloped in the fastener base 8. The nested assembly 1 shown in FIG. 3 is now pre-assembled and ready for use with a bone screw 14 and cooperating rod 18. As illustrated in FIG. 3, in such a pre-assembly arrangement, the V-ring 80 preferably projects beyond the point 82 and V-ring 84 of the set screw 6, such that the base 8 will seat fully within the bone screw arms 28 prior to engagement of the set screw 6 with the rod 18.

With reference to FIGS. 4–7, at least two and up to a plurality of bone screws 14 are installed into respective, selected vertebra 24. Each of the bone screws 14 are preferably pre-assembled by loading the shank 22 into the head 14, downloading the retainer ring 40 through the channel 16, rotatably threading and securing the ring 40 onto the capture portion 34 and inserting the insert 44 at a side of the bone screw head 12 at a position to allow the shank 22 to freely swivel with respect to the head 12.

Each of the vertebra 24 may be pre-drilled to minimize stressing the bone and have a guide wire (not shown) to provide a guide for the placement and angle of the shank 22 with respect to the vertebra 24. A further tap hole may be made using a tap with the guide wire as a guide. Then, a bone screw 14 is threaded onto the guide wire utilizing the cannulation bore 48 by first threading the wire into a bottom of the shank 22 and then out of the capture portion 34. The shank 22 is then driven into the vertebra 24 by a tool (not shown), engaging the slot 42 disposed on the retainer ring 40, using the wire as a placement guide.

Figure 4:
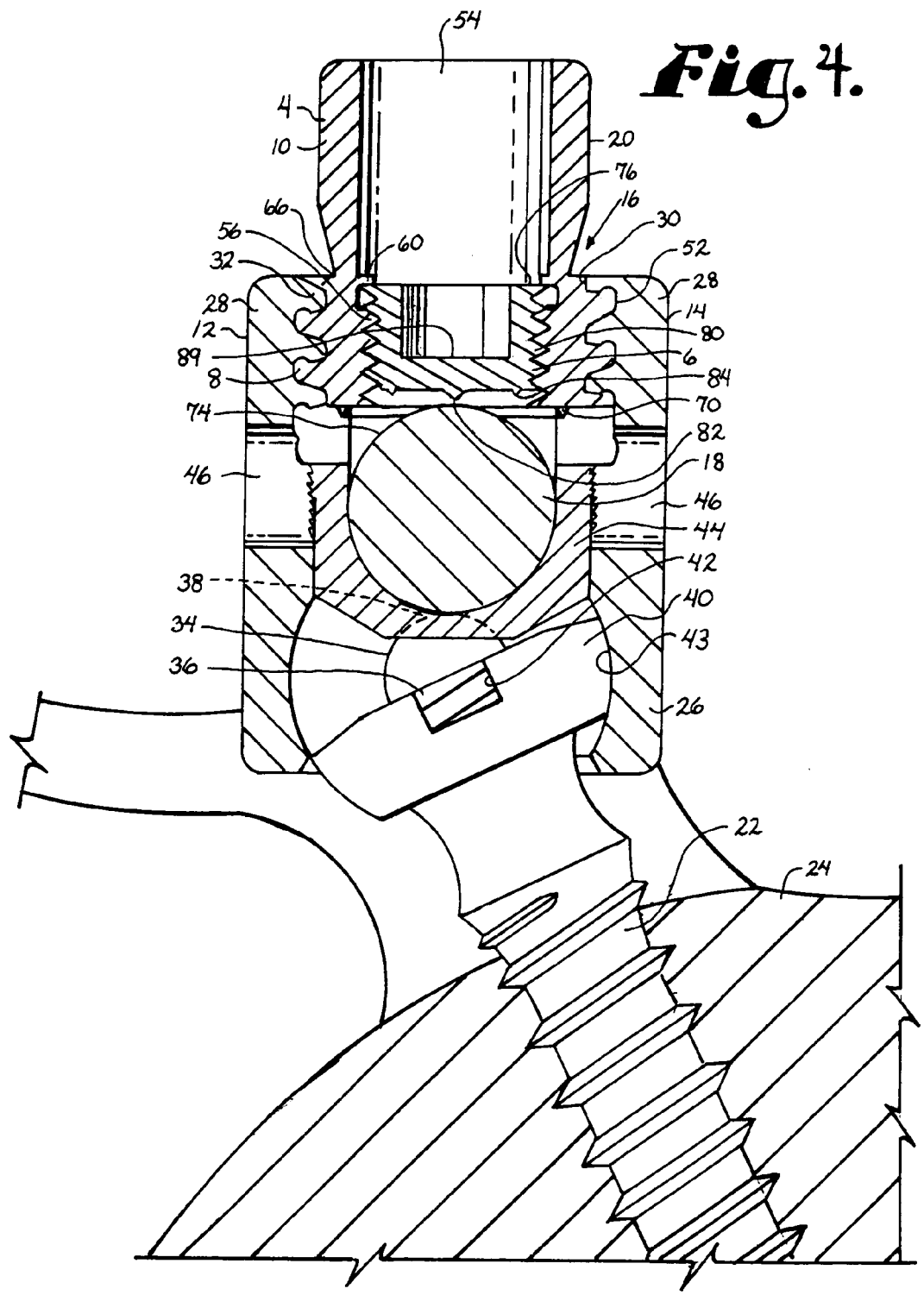
FIG. 4 is a reduced cross-sectional view of the assembly of FIG. 3 shown received in a bone screw head and engaging a rod.

With reference to FIG. 4, the rod 18 is eventually positioned within the head open channel 16, of each of the bone screws 14. If desired, the insert 44 is utilized to set the angle of articulation between the shank 22 and the head 12 prior to rod insertion. After the rod 18 is positioned in the bone screw heads 12, a nested fastener assembly 1 is inserted into and advanced between the arms 28 of each bone screw head 12 by rotating the fastener 4, using the installation tool 21 engaged with the surfaces 20 of the break-off head 10. The fasteners 4 are then tightened, preferably in a selected order, by further turning of the tool 21, with or without bending of the rod 18 in order to achieve and maintain a desired alignment of the spine. As each fastener 4 is tightened, the respective break-off head 10 is twisted by the tool 21 to a preselected torque, for example 90 to 120 inch pounds, causing the head 10 to break off as shown in FIG. 5.

With reference to FIG. 6, thereafter, the set screws 6 are tightened, preferably in a selected order, by inserting the Allen-type tool 90 into the aperture 86 and rotating the tool 90 to thread the set screw 6 downwardly toward the rod 18. As each set screw 6 is torqued tightly using the tool 90, first the point 82 and then portions of the V-ring 84 preferably come into contact and abrade or dig into the rod surface 74.

As previously discussed herein, because the rod 18 may be bent, not all projected portions of the fastener base 8 and the set screw 6 may come into contact with the rod 18. The availability of multiple locations of engagement of the fastener base 8 and the set screw 6 with the rod 18 increases the probability that the rod 18 will be engaged securely by the nested fastener assembly 1. It is noted that the fastener base 8 may only seat at the bottom of the bone screw head opening 16 so as to close the opening 16 and capture the rod 18 therein without the V-ring 70 or the base 68 contacting the rod surface 74. The set screw 6 is then turned and tightened against the rod 18, the point 84 engaging the rod surface 74 and thereby securing the rod 18 in place.

With reference to FIG. 7, if removal of the assembly 1 is necessary, or if it is desired to release the rod 18 at a particular location, disassembly is accomplished by using the Allen-type driving tool 90, mated with the set screw 6 at the aperture 86 and turned in a direction to rotate the set screw 6 up and out of the base 8. The set screw top 76 then backs into and abuts the abutment shoulder 60, transferring rotational torque exerted from the tool 90 from the set screw 6 to the fastener base 8. The base 8 then rotates with the guide and advancement structure 52 threading out of the guide and advancement structure 32 of the head 12. Thus, both the set screw 6 and the fastener base 8 are removed from the bone screw head 12 as a single unit. If necessary, disassembly of the rod 18 and bone screw 14 may be accomplished in reverse order to the procedure described previously herein for assembly.

With reference to FIGS. 8–12, the reference number 100 generally represents a second or alternative embodiment of a nested fastener assembly according to the present invention. With particular reference to FIGS. 8–11, the assembly 100 includes a fastener 104 and an uploaded set screw 106.

Figure 12:
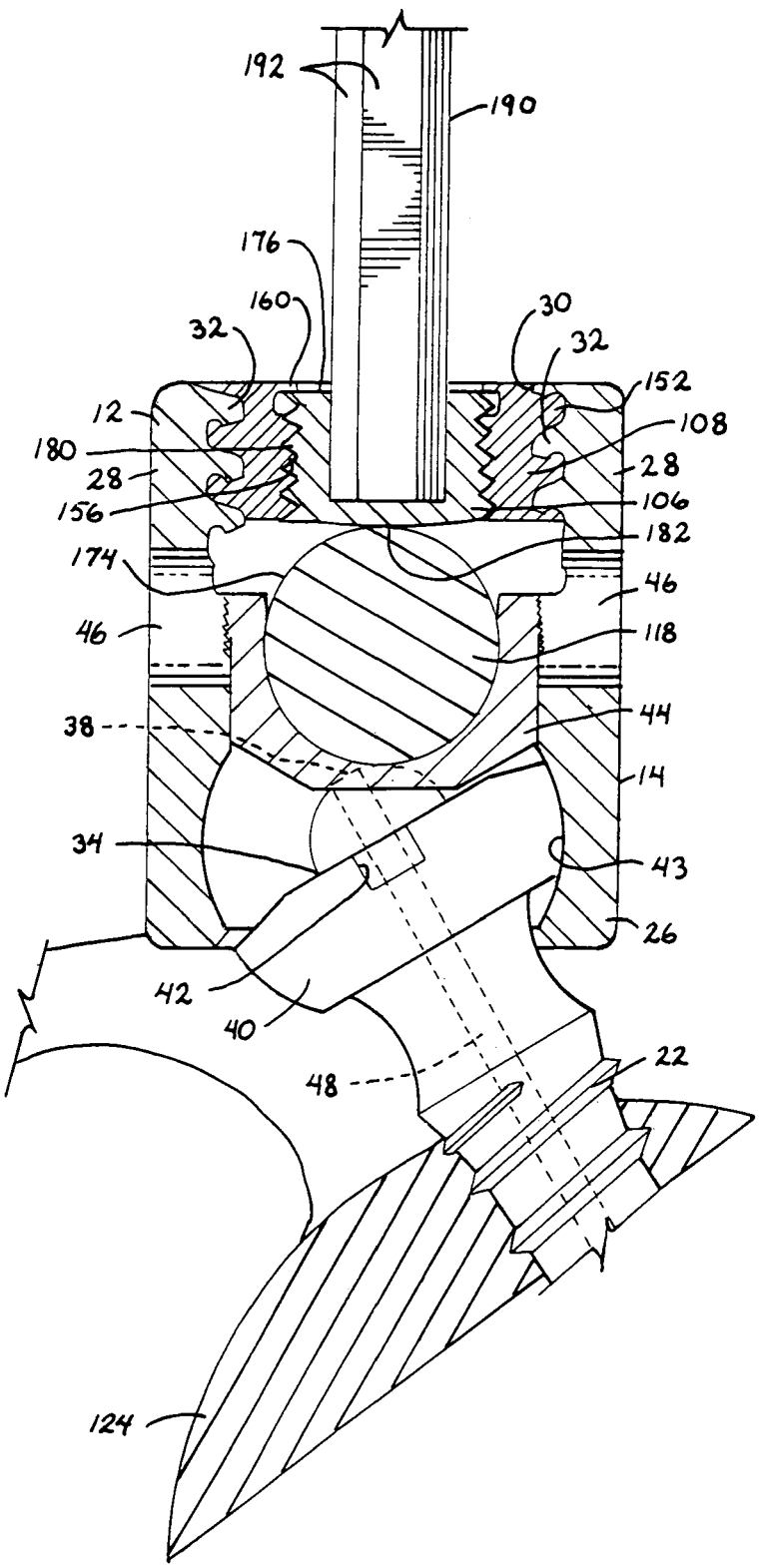
FIG. 12 is a reduced cross-sectional view of the assembly of FIG. 10 shown received in a bone screw head, engaging a rod, the break-off head of the fastener having been removed and further showing engagement with a set screw tool.

The fastener 104 includes a base 108 integral or otherwise attached to a break-off head 110. The base 108 cooperates with the head 12 of the bone screw 14 to close the open channel 16 bounded by the arms 28, and to clamp a spinal fixation rod 118 within the head 12 as illustrated in FIG. 12 and also illustrated in FIGS. 4–7 and described previously herein with respect to the nested fastener assembly 1. Thus, the description of the bone screw 14 already described herein is also incorporated by reference with respect to the fastener assembly 100. It is noted that although shown cooperating with the bone screw 14, the nested implant fastener assembly 100 of the present invention can be used with virtually any type of open-ended bone screw, including fixed monoaxial and polyaxial bone screws of many different types wherein the head is locked relative to the shank by structure other than in the manner described in the illustrated embodiment.

The break-off installation head 110 includes a faceted outer surface 120 sized and shaped for engagement with an installation tool (not shown), similar to the tool 21 shown in FIG. 5 for installing the fastener 4 to the bone screw 14. Likewise, the installation tool engages the outer surface 120 of the break-off head 110 to install the fastener 104 to the bone screw 14 and thereafter separate the break-off head 110 from the base 108 when installation torque exceeds selected levels.

The base 108 of the fastener 104 is substantially cylindrical, having an axis of rotation A' and an external surface 150 having a guide and advancement structure 152 disposed thereon. The guide and advancement structure 152 is matingly attachable to the guide and advancement structure 32 of the bone screw head 12. As with the guide and advancement structure 32, the guide and advancement structure 152 can be of any type, including V-type threads, buttress threads, reverse angle threads, or square threads. Preferably the guide and advancement structure 152 is a helically wound flange form that interlocks with the reciprocal flange form as part of the guide and advancement structure 32 on the interior of the bone screw arms 28. The guide and advancement structures 32 and 152 are preferably of a type that do not exert radially outward forces on the arms 28 and thereby avoid tendencies toward splaying of the arms 28 of the bone screw head 12, when the fastener 104 is tightly torqued into the head 12.

The fastener 104 includes an internal, centrally located through-bore 154. At the base 108, the bore 154 is substantially defined by a guide and advancement structure, shown in FIGS. 9, 10 and 12 as an internal V-shaped thread 156. The thread 156 is sized and shaped to receive the threaded set screw 106 therein as will be discussed in more detail below. Although a traditional V-shaped thread 156 is shown, it is foreseen that other types of helical guide and advancement structures may be used. Near a substantially annular planar top surface 158 of the base 108, an abutment shoulder 160, extends uniformly radially inwardly. The abutment shoulder 160 is spaced from the V-shaped thread 156 and sized and shaped to be a stop for the set screw 106, prohibiting the set screw 106 from advancing out of the top 158 of the base 108. An inner cylindrical wall 162 separates the abutment shoulder 160 from the thread 156. The cylindrical wall 162 has a diameter slightly greater than a root or major diameter of the internal thread 156. The wall 162 partially defines a cylindrical space or passage 164 for axial adjustable placement of the screw 106 with respect to the rod 118 as will be discussed in more detail below.

The fastener 104 further includes the break-off head 110 that is integral or otherwise attached to the fastener 104 at a neck or weakened region 166. The neck 166 is dimensioned in thickness to control the torque at which the break-off head 110 separates from the fastener 104. The preselected separation torque of the neck 166 is designed to provide secure clamping of the rod 118 by the fastener 104 before the head 110 separates. For example, 120 inch pounds of force may be a selected break-off torque. The illustrated, hexagonal faceted surfaces 120 of the break-off head 110 enables positive, non-slip engagement of the head 110 by the installation and torquing tool (not shown). Separation of the break-off head 110 leaves only the more compact base 108 of the fastener 104 installed in the bone screw head 112, so that the installed fastener 104 has a low profile.

In the embodiment of the assembly 100 shown in the drawing figures, the base 108 of the fastener 104 has a substantially flat, smooth, bottom surface 168. The surface 168 preferably does not come into contact with an outer surface 174 the rod 118 when fully installed as shown in FIG. 12. It is foreseen that clamp enhancing structure, such as the ring 70 described with respect to the assembly 1 or surface treatment such as knurling may be employed on the bottom surface 168, useful, for example, if a portion of a bent rod comes into contact therewith.

The uploadable set screw 106 has a substantially planar top 176 and a bottom 177. The screw 106 is substantially cylindrical in shape, having a centrally located axis of rotation B' and an outer cylindrical surface 178 with a V-shaped thread 180 extending from the top 176 to the bottom 177 thereof. The surface 178 and thread 180 are sized and shaped to be received by and mated with the inner thread 156 of the fastener base 108 in a nested relationship. In such relationship, the axis B' is operably the same as the axis A' of the fastener base 108.

Figure 9:
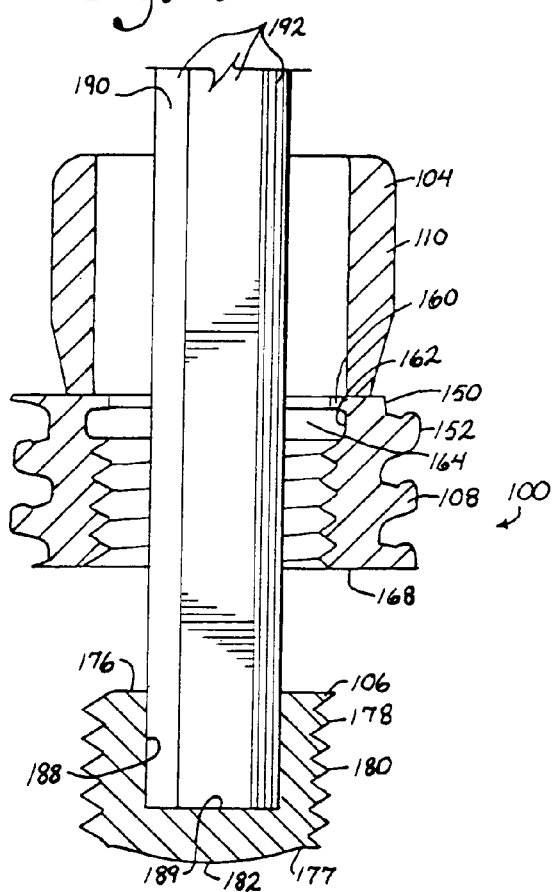
FIG. 9 is an enlarged cross-sectional view taken along the line 9—9 of FIG. 8 and shown with a set screw tool.
Figure 10:
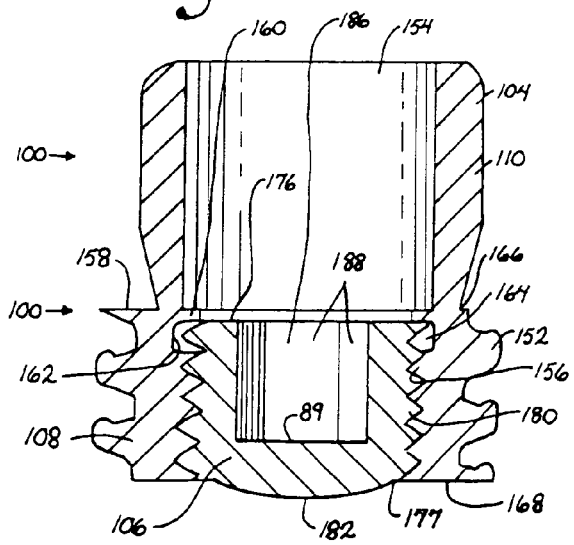
FIG. 10 is a cross-sectional view similar to FIG. 9, showing the set screw inserted in the fastener.
Figure 11:
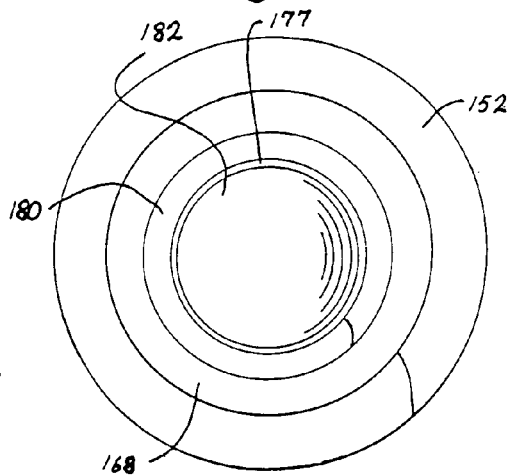
FIG. 11 is a bottom plan view of the fastener and inserted set screw of FIG. 10.

The bottom 177 of the set screw 106, best illustrated in FIGS. 8–11, includes a radially extending convex, curved, partially spherical or dome-shaped interference or compressive structure 182, preferably having a substantially uniform radius to provide for positive engagement with the rod 118 at the surface 174. With particular reference to FIG. 11, the domed structure 182 projects from the bottom 177 of the set screw 106 at a greatest distance along the central axis B'. The illustrated domed structure 182 has a uniform or constant radius of generation. However, it is foreseen that in certain embodiments the radius may vary depending upon the needs and desires of the particular structure and the dome 182 may have a shape that is only partly a spherical curved surface or some other shape. The dome 182 may simply be a curved surface that allows greatest projection along the axis. That is, the dome surface could be radiused at the location of greatest projection and feathered along a periphery thereof so as to not have a continuous uniform radius of generation throughout but rather a continually changing radius of generation along at least the length thereof. Preferably, the dome 182 is smoothly curved where the dome 182 intersects with the axis B'. The domed structure 182 is designed to securely frictionally engage the rod surface 174 at almost any orientation of the rod 118 with respect to the set screw 106, as the rod 118 may be straight or bent at the location of engagement between the rod 118 and the set screw 106. The curved structure 182 exerts compressive force along the central axis B' of the set screw 106 when an apex of the structure 182 is in frictional engagement with the rod 118. It is foreseen that other structures for enhancing clamping and surface treatments, such as knurling or the like may be used in some embodiments or none in others.

The set screw 106 includes a central aperture 186 formed in the top 176 and defined by faceted side walls 188 and a hexagonal bottom seating surface 189, forming a hexshaped internal drive for positive, non-slip engagement by a set screw installment and removal tool such as an Allen-type wrench 190 as depicted in FIGS. 9 and 12. With reference to FIG. 9, the central aperture 186 cooperates with the central internal bore 154 of the fastener 104 for accessing and uploading the set screw 106 into the fastener 104 prior to engagement with the bone screw 14. After the assembly 100 engages the bone screw head 12, and the break-off head 110 is broken off, the tool 190 is used to set and lock the set screw domed projection 182 against the rod 118 as illustrated in FIG. 12.

If it is desirable or necessary to release the rod 118 from the bone screw 14, the tool 190 may be used to remove both the set screw 106 and attached fastener base 108 as a single unit, with the set screw 106 contacting and contained within the base 108 by the abutment shoulder 160. Thus, rotation of the tool 190 engaged with the set screw 106 backs both the set screw 106 and the fastener base 108 out of the guide and advancement structure 32 in the arms 28 of the bone screw head 12, thereby releasing the rod 118 for removal from the bone screw 14 or repositioning of the rod 118. It is foreseen that other removal structures such as side slots or other screw receiving and engagement structures may be used to engage the set screw 106 that is nested in the fastener base 108.

In use, the set screw 106 is assembled with the fastener 104 prior to insertion in the bone screw head 12. With reference to FIG. 9, the Allen-type tool 190 is inserted through the bore 154 of the fastener 104 and into the aperture 186 of the set screw 106 until seated on the bottom surface 189, with faceted outer surfaces 192 of the tool 190 engaging the inner faceted walls 188 of the set screw 106. The set screw 106 is then uploaded into the fastener 104 by rotation of the set screw 106 with respect to the fastener 104 to mate the set screw thread 180 with the fastener inner thread 156 until the set screw top surface 176 abuts the abutment shoulder 160, resulting in the nested arrangement of the assembly 100 shown in FIG. 10, with the set screw 106 enveloped in the fastener base 108, with the exception of the domed projection 182 that projects downwardly from the bottom 168 of the base 108. The nested assembly 100 shown in FIG. 10 is now pre-assembled and ready for use with a bone screw 14 and cooperating rod 118.

With reference to FIG. 12, as previously described herein, and incorporated by reference with respect to the assembly 100, the bone screws 14 are preferably pre-assembled, driven into respective vertebra 124 and the rod 118 is eventually positioned within the head open channel 16 of each of the bone screws 14. If desired, the insert 44 is utilized to set the angle of articulation between the shank 22 and the head 12 prior to rod insertion.

After the rod 118 is positioned in the bone screw heads 12, a nested fastener assembly 100 is inserted into and advanced between the arms 28 of each bone screw head 12 by rotating the fastener 104, using the installation tool (not shown) engaged with the surfaces 120 of the break-off head 110. The fasteners 104 are then tightened, preferably in a selected order, by further turning of the installation tool, with or without bending of the rod 118, in order to achieve and maintain a desired alignment of the spine. As each fastener 104 is tightened so as to bias or push the domed structure 182 against the rod 118, the respective break-off head 110 is twisted by the tool to a preselected torque, for example 90 to 120 inch pounds, causing the head 110 to break off. With reference to FIG. 12, further tightening is accomplished by advancing the set screws 106 downwardly against the rod 118 by inserting the Allen-type tool 190 into the aperture 186 and rotating the tool 190 to thread the set screw 106 toward the rod 118, frictionally engaging the dome-shaped structure 182 with the rod 118.

If removal of the assembly 100 is necessary, or if it is desired to release the rod 118 at a particular location, disassembly is accomplished by using the Allen-type driving tool 190, mated with the set screw 106 at the aperture 186 and turned in a direction to rotate the set screw 106 up and out of the base 108. The set screw top 176 may already be in abutment with the shoulder 160 or slightly spaced therefrom. Thus, rotation of the driving tool 190 may first back the screw 106 up against the shoulder 160, and then rotates the engaged screw 106 and base 108 as a single unit out of the guide and advancement structure 32 of the head 12.

Figure 13:
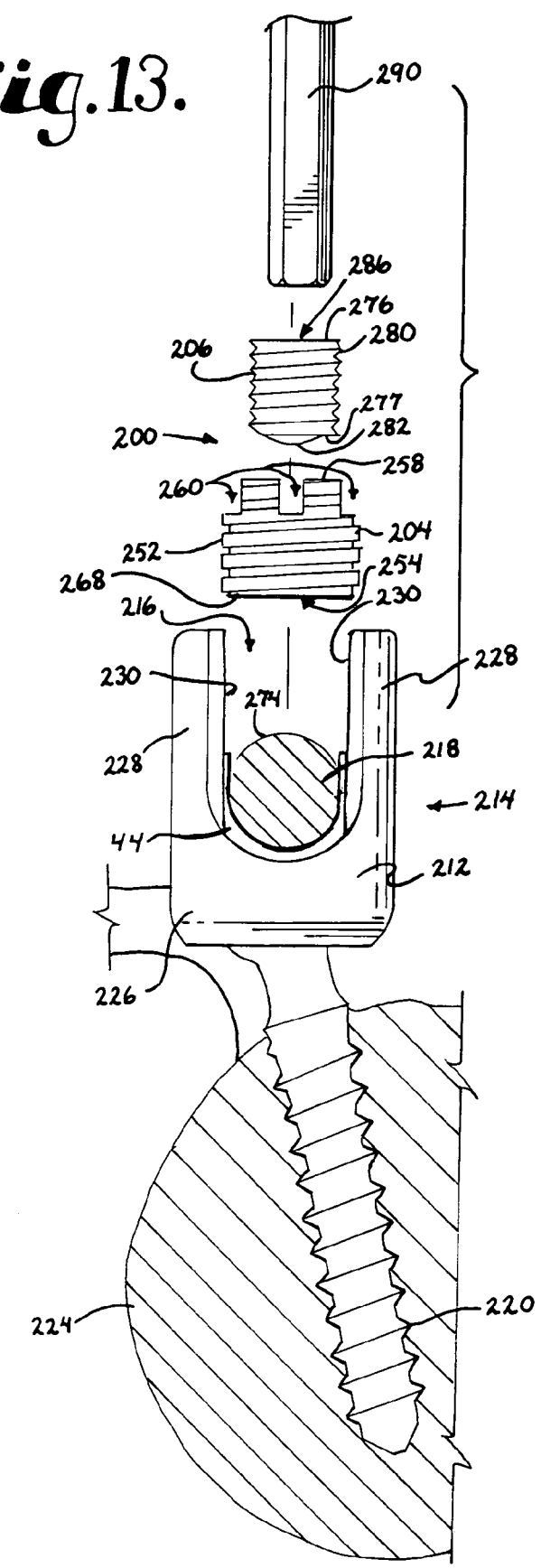
FIG. 13 is an exploded perspective view of a third embodiment of an assembly according to the invention including a fastener and an inner set screw and further showing a rod, a bone screw implanted in a vertebra and a set screw tool.

With reference to FIG. 13, the reference numeral 200 generally designates a third embodiment of a nested implant fastener assembly according to the present invention. The assembly 200 includes a fastener base 204 and a set screw 206 that may be downloaded or uploaded, but is preferably downloaded as indicated in FIG. 13. The fastener base 204 cooperates with a head 212 of a bone screw, generally 214, as illustrated in FIG. 13, to close an open channel 216 formed by the head 212 and to clamp a spinal fixation rod 218 within the bone screw head 212.

Also, as illustrated in FIG. 13, one kind of bone screw 214 for use with the fastener assembly 200 includes a threaded shank 220 for implanting or anchoring in a bone such as a vertebra 224. The threaded shank 220 of the bone screw 214 is pivotally attached to the substantially cylindrically shaped head 212 that includes a base 226 and spaced arms 228 that define the open U-shaped channel 216 for receiving the rod 218 or other elongate spinal fixation structure. The rod receiving channel 216 is sized so that the rod 218 fits snugly therein to maximize clamping or frictional engagement of the rod 218 with surfaces forming the channel 216.

Each of the arms 228 has an interior surface 230 that defines an inner substantially cylindrical profile and includes a partial, helically wound guide and advancement structure (not shown) similar to the structure 32 of the bone screw head 12 illustrated in FIGS. 4–7 and incorporated by reference herein. Although not shown, the bone screw shank 220 includes an upper capture structure identical or similar to the bone screw 14 for pivotally attaching the shank 220 to the bone screw head 212. Thus, the structure previously described herein with respect to the bone screw 14 is incorporated by reference with respect to the bone screw 214. It is noted that the nested implant fastener assembly 200 of the present invention can be used with virtually any type of open-ended bone screw, including fixed monoaxial and polyaxial bone screws of many different types wherein the head is locked relative to the shank by structure other than in the manner described with respect to the bone screws 14 and 214.

The fastener base 204 is substantially cylindrical and has an external surface with a guide and advancement structure 252 disposed thereon. The guide and advancement structure 252 is matingly attachable to the guide and advancement structure disposed on the inner surfaces 230 of the bone screw head 212. The guide and advancement structure 252 can be of any type, including V-type threads, buttress threads, reverse angle threads, or square threads. Preferably the guide and advancement structure 252 is a helically wound flange form that interlocks with the reciprocal flange form as part of the guide and advancement structure on the interior 230 of the bone screw arms 228. The mating guide and advancement structures are preferably of a type that do not exert radially outward forces on the arms 228 and thereby avoid tendencies toward splaying of the arms 228 of the bone screw head 212, when the fastener base 204 is rotated and tightened into the head 212.

The fastener base 204 includes an internal, centrally located through-bore 254 substantially defined by a guide and advancement structure (not shown) that is preferably an internal V-shaped thread similar to the thread 56 of the base 8 of the assembly 1 according to the invention, the description of which is incorporated by reference herein. The inner thread is sized and shaped to receive the threaded set screw 206 therein as will be discussed in more detail below. Although a traditional V-shaped thread is preferred, it is foreseen that other types of helical guide and advancement structures may be used. Near a top surface 258 of the fastener base 204, a pair of transverse slots 260 disposed perpendicular to one another provide driving surfaces for positive, non-slip engagement with an installation tool (not shown) for rotatingly installing the fastener base 204 into the bone screw head 212 as will be described in more detail below. Similar to the base 108 of the nested set screw 100, previously described herein, the fastener base 204 has a bottom 268 that is substantially flat and smooth and is designed to close the channel 216 and preferably remain spaced from the rod 218, with the inner set screw 206 designed to engage a surface 274 of the rod 218 as will be further described herein.

The set screw 206 has a substantially planar top 276 and a bottom 277. The set screw 206 is substantially cylindrical in shape and includes an outer cylindrical surface with a V-shaped thread 280 extending from the top 276 to the bottom 277 thereof. The thread 280 is sized and shaped to be received by and mated with the inner thread (not shown) defining the bore 254 of the fastener base 204 in a nested relationship.

The bottom 277 of the set screw 206 further includes a radially extending, convex, curved, partially spherical or dome-shaped structure 282, preferably having a substantially uniform radius to provide for positive engagement with the rod 218 at the surface 274. The domed structure 282 is similar to the domed structure 182 previously described with respect to the assembly 100 and such description is incorporated by reference herein with respect to the domed structure 282. The domed structure 282 projects centrally from the bottom 277 of the set screw 206 and is designed to securely frictionally engage the rod surface 274 at almost any orientation of the rod 218 with respect to the set screw 206, as the rod 218 may be straight or bent or skewed with respect to the bone screw head 212 at the location of engagement between the rod 218 and the set screw 206. The domed structure 282 exerts compressive force along a central axis of the set screw 206 when the structure 282 is in frictional engagement with the rod 218. It is foreseen that other structures for enhancing clamping, including surface treatments such as knurling or the like may be used in some embodiments or none in others.

The set screw 206 includes a central aperture 286 formed in the top 276 and defined by faceted side walls and a hexagonal bottom seating surface, forming a hex-shaped internal drive for positive, non-slip engagement by a set screw installment and removal tool such as an Allen-type tool 290. The tool 290 is used to load the set screw 206 into the fastener base 204 after installation of the fastener base 204 into the bone screw head 212. Alternatively, the set screw 206 may be pre-loaded into the fastener base 204 prior to installation of the fastener base 204 into the bone screw head 212. In either procedure, the tool 290 is used in a final tightening step to frictionally engage the set screw domed surface 282 against the rod 218. The tool 290 is also used for removal purposes as described more fully below.

In use, as previously described herein with respect to the assemblies 1 and 100, and incorporated by reference with respect to the assembly 200, the bone screws 214 are preferably pre-assembled, driven into respective vertebra 224 and the rod 218 is eventually positioned within the head open channel 216 of each of the bone screws 214. If desired, a top- or side-loading insert may be positioned in the bone screw head 212 and utilized in some way to set the angle of articulation between the threaded shank 220 and the head 212, for example, prior to rod insertion or after rod insertion.

After the rod 218 is positioned in the bone screw heads 212, a fastener base 204 is first inserted over the channel 216 of each bone screw head 212 and rotated into engagement with the bone screw 214 between the arms 228 of the bone screw head 212 to close off the channel 216 utilizing the installation tool (not shown) that engages the fastener base 204 at the transverse slots 260. The installation tool (not shown) is turned until each fastener base 204 is completely disposed between the arms 228 of a respective bone screw head 212 and torqued until tightened therein. Then, the set screw 206 is inserted over the bore 254 of each fastener base 204 with the Allen-type tool 290 received in the central aperture 286 of the set screw 206. The tool 290 is seated within the aperture 286 and turned to rotate and drive the set screw 206 into the threaded bore 254 of the fastener base 204, mating the thread 280 with the thread defining the bore 254 until the domed structure 282 projects from the bottom 268 of the fastener base 204 and frictionally engages the surface 274 of the rod 218, securing the rod 218 within the bone screw head 212.

Alternatively, each of the set screws 206 may be assembled with a respective fastener base 204 prior to insertion in the bone screw head 212. The Allen-type tool 290 is inserted into the aperture 286 of the set screw 206 until seated therein and turned to rotate and drive the set screw 206 into the threaded bore 254 of the fastener base 204 until the domed structure 282 is flush with or projects slightly from the bottom 268 of the fastener base 204. The nested fastener assembly 200 may then be inserted into and advanced between the arms 228 of each bone screw head 212 by rotating the fastener base 204, using the installation tool (not shown) engaged with the fastener base 204 at the transverse slots 260. Each fastener base 204 is tightened by further turning of the installation tool. Then, the set screws 206 are further advanced downwardly against the rod 218 by inserting the Allen-type tool 290 into the aperture 286 and rotating the tool 290 to further thread the set screw domed bottom 282 toward the rod 218 and into engagement therewith.

If removal of the assembly 200 is necessary, disassembly is accomplished by using the Allen-type tool 290 mating with the set screw 206 at the aperture 286 to rotate the set screw 206 and reverse the advancement thereof in the fastener base 204. Subsequently, the fastener base 204 is loosened by mating the slots 260 with the installation tool (not shown) to reverse the advancement of the fastener base 204 in the arms 228 of the bone screw 214. It may be possible to loosen both the set screw 206 and the fastener base 204 with the Allen-type tool 290, thus loosening the assembly 200 as a single unit, as the fastener base 204 and inner set screw 206 may be joined together by threads at the lower ends thereof becoming deformed by engagement with the rod 218.

It is to be understood that while certain forms of the present invention have been illustrated and described herein, it is not to be limited to the specific forms or arrangement of parts described and shown.

What is claimed and desired to be secured by Letters Patent is as follows:

1. A nested fastener and set screw combination for securing a structural element within a receiver of a medical implant, the receiver having an opening, the combination comprising:
   a) a fastener adapted to be interferingly positioned within the opening of the receiver so as to close the opening when in an installed configuration, the fastener having a through bore extending from a first end to a second end, the bore defined in part by a first guide and advancement structure;
   b) a set screw having a second guide and advancement structure rotatingly mateable with the first guide and advancement structure, the set screw loadable and receivable in the bore of the fastener through the first end, the set screw having a setting configuration wherein the set screw is in engagement with the structural element; and
   c) an abutment shoulder located on said fastener and extending into said bore so as to interferingly prohibit advancement of the set screw out of the second end.

2. A nested fastener and set screw assembly for operably securing a rod within a bone screw head, the head having an opening, the assembly comprising:
   a) a fastener having a first end, a second end and an abutment shoulder disposed near the second end, the fastener adapted to be interferingly positioned within the bone screw head opening when in an installed configuration, the fastener having a centrally located through bore extending from the first end to the second end and a helical thread partially defining the through bore;
   b) a break-off head connected to and coaxial with the fastener, the break-off head operably breaking from the fastener at a preselected torque;
   c) a threaded set screw rotatably mateable with the helical thread of the fastener and receivable into the bore at the first end, the abutment shoulder interferingly prohibiting advancement of the set screw out of the second end; and
   d) an interference structure disposed on the set screw shaped and positioned to provide compressive force along a central axis of the set screw when in a setting configuration wherein the interference structure is in frictional engagement with the rod.

3. The combination of claim 2 wherein the abutment shoulder projects from the fastener inwardly into the bore.

4. The combination of claim 3 wherein the abutment shoulder is annular.

5. The combination of claim 2 wherein the set screw interference structure is a pointed projection shaped and positioned to operably cut into a surface of the rod in the setting configuration.

6. The combination of claim 2 wherein the set screw interference structure is curved and substantially convex.

7. The combination of claim 2 wherein the set screw interference structure is partially spherical.

8. The combination of claim 2 wherein the fastener includes an external guide and advancement structure that rotatingly operably cooperates with complementary structure defining the bone screw head opening to interferingly position the fastener within the opening.

9. The combination of claim 8 wherein the fastener external guide and advancement structure is a helically wound flange form.

10. The combination of claim 2 wherein the set screw has a tool engagement formation adapted for non-slip engagement of the set screw by a set screw installment and removal tool.

11. The combination of claim 10 wherein the set screw tool engagement formation and the abutment shoulder are configured to provide for simultaneous removal of the set screw and the fastener from the receiver opening.

12. A nested fastener and set screw combination for securing a structural element within a receiver of a medical implant, the receiver having an opening, the combination comprising:
   a) a fastener adapted to be interferingly positioned within the opening of the receiver so as to close the opening when in an installed configuration, the fastener having an inner guide and advancement structure defining a bore extending therethrough;
   b) a set screw having an outer guide and advancement structure rotatingly mateable with the inner guide and advancement structure for loading and receiving the set screw in the bore of the fastener; and
   c) a curved, substantially convex interference structure projecting from a base of the set screw shaped and positioned to provide compressive force along a central axis of the set screw when in a setting configuration wherein the interference structure is in frictional engagement with the structural element.

13. The combination of claim 12 wherein the set screw is one of uploadable and downloadable in the fastener.

14. The combination of claim 12 wherein the interference structure is partially spherical.

15. The combination of claim 12 wherein the fastener includes an external guide and advancement structure that rotatingly operably cooperates with complementary structure defining the receiver opening to interferingly position the fastener within the opening.

16. The combination of claim 15 wherein the fastener external guide and advancement structure is a helically wound flange form.

17. The combination of claim 12 wherein the set screw has a tool engagement formation adapted for non-slip engagement of the set screw by a set screw installment and removal tool.

18. The combination of claim 12 wherein the fastener has a tool engagement formation adapted for non-slip engagement of the fastener by a fastener installment and removal tool.

19. In a fastener and set screw combination wherein the fastener is adapted to close an opening in a medical implant and capture a structural member therein and wherein the fastener includes a top, a bottom and a central bore with a set screw received in the bore; the improvement comprising:
   a) a curved, substantially convex interference structure projecting from a base of the set screw, the interference structure shaped and positioned to provide compressive force along a central axis of the set screw when in a setting configuration wherein the interference structure is in frictional engagement with the structural element.

20. The improvement of claim 19 wherein the interference structure is partially spherical.

21. A medical implant assembly method comprising the steps of:

a) up-loading a set screw into a threaded bore of a fastener by inserting the set screw into a bottom of the fastener bore;
b) rotating the set screw with respect to the fastener until the set screw is fully nested in the fastener and abuts an abutment shoulder near a top of the bore
c) inserting the nested fastener and set screw into an opening of a medical receiver; d) rotating the fastener at a break-off head thereof until the head breaks from the fastener at a preselected torque; and e) driving the set screw by rotation into engagement with a structural element.

22. A nested fastener and set screw combination for securing a structural element within a receiver of a medical implant, the receiver having an opening, the combination comprising:
  a) a fastener adapted to be interferingly positioned within the opening of the receiver so as to close the opening when in an installed configuration, the fastener having a through bore extending from a first end to a second end, the bore defined in part by a first guide and advancement structure;
  b) a set screw having a second guide and advancement structure rotatingly mateable with the first guide and advancement structure, the set screw loadable and receivable in the bore of the fastener through the first end, the set screw having a setting configuration wherein the set screw is in engagement with the structural element; and
  c) an abutment shoulder interferingly prohibiting advancement of the set screw out of the second end wherein the abutment shoulder projects from the fastener inwardly into the bore and is disposed near the second end.

23. The combination of claim 22 wherein the abutment shoulder is annular.

24. The combination of claim 22 wherein the fastener includes an external guide and advancement structure that rotatingly operably cooperates with complementary structure defining the receiver opening to interferingly position the fastener within the opening.

25. The combination of claim 24 wherein the fastener external guide and advancement structure is a helically wound flange form.

26. The combination of claim 22 wherein the fastener has an interference structure shaped and positioned to operably cut into a surface of the structural element in the installed configuration.

27. The combination of claim 22 wherein the set screw has a tool engagement formation adapted for non-slip engagement of the set screw by a set screw installment and removal tool.

28. A nested fastener and set screw combination for securing a structural element within a receiver of a medical implant, the receiver having an opening, the combination comprising:
  a) a fastener adapted to be interferingly positioned within the opening of the receiver so as to close the opening when in an installed configuration, the fastener having a through bore extending from a first end to a second end, the bore defined in part by a first guide and advancement structure;
  b) a set screw having a second guide and advancement structure rotatingly mateable with the first guide and advancement structure, the set screw loadable and receivable in the bore of the fastener through the first end, the set screw having a setting configuration wherein the set screw is in engagement with the structural element and wherein the set screw has a base and an interference structure projecting from the base, the interference structure shaped and positioned to operably cut into a surface of the structural element in the setting configuration; and
  c) an abutment shoulder interferingly prohibiting advancement of the set screw out of the second end.

29. The combination of claim 28 wherein the interference structure is a pointed projection.

30. The combination of claim 29 wherein the interference structure projects from the base at a central axis of rotation of the set screw.

31. A nested fastener and set screw combination for securing a structural element within a receiver of a medical implant, the receiver having an opening, the combination comprising:
  a) a fastener adapted to be interferingly positioned within the opening of the receiver so as to close the opening when in an installed configuration, the fastener having a through bore extending from a first end to a second end, the bore defined in part by a first guide and advancement structure;
  b) a set screw having a second guide and advancement structure rotatingly mateable with the first guide and advancement structure, the set screw loadable and receivable in the bore of the fastener through the first end, the set screw having a setting configuration wherein the set screw is in engagement with the structural element; said set screw having a base and a curved substantially convex structure projecting from the base along a central axis of the set screw; and
  c) an abutment shoulder interferingly prohibiting advancement of the set screw out of the second end;
    The combination of claim 1 wherein the set screw has a base and a curved substantially convex structure projecting from the base along a central axis of the set screw.

32. The combination of claim 31 wherein the substantially convex structure is partially spherical.

33. A nested fastener and set screw combination for securing a structural element within a receiver of a medical implant, the receiver having an opening, the combination comprising:
  a) a fastener adapted to be interferingly positioned within the opening of the receiver so as to close the opening when in an installed configuration, the fastener having a through bore extending from a first end to a second end, the bore defined in part by a first guide and advancement structure;
  b) a set screw having a second guide and advancement structure rotatingly mateable with the first guide and advancement structure, the set screw loadable and receivable in the bore of the fastener through the first end, the set screw having a setting configuration wherein the set screw is in engagement with the structural element; the set screw having a tool engagement formation adapted for non-slip engagement of the set screw by a set screw installment and removal tool;
  c) an abutment shoulder interferingly prohibiting advancement of the set screw out of the second end;
    The combination of claim 1 wherein the set screw has a base and a curved substantially convex structure projecting from the base along a central axis of the set screw; and d) the set screw tool engagement formation and the abutment shoulder being configured to provide for simultaneous removal of the set screw and the fastener from the receiver opening.

34. A nested fastener and set screw combination for securing a structural element within a receiver of a medical implant, the receiver having an opening, the combination comprising:
- a) a fastener adapted to be interferingly positioned within the opening of the receiver so as to close the opening when in an installed configuration, the fastener having a through bore extending from a first end to a second end, the bore defined in part by a first guide and advancement structure;
- b) a set screw having a second guide and advancement structure rotatingly mateable with the first guide and advancement structure, the set screw loadable and receivable in the bore of the fastener through the first end, the set screw having a setting configuration wherein the set screw is in engagement with the structural element;
- c) an abutment shoulder interferingly prohibiting advancement of the set screw out of the second end;

The combination of claim 1 wherein the set screw has a base and a curved substantially convex structure projecting from the base along a central axis of the set screw; and
- d) a fastener break-off head connected to and coaxial with the fastener, the break-off head adapted to operably break from the fastener at a preselected torque.

35. In a fastener and set screw combination wherein the fastener is adapted to close an opening in a medical implant and capture a structural member therein and wherein the fastener includes a top, a bottom and a central bore with a set screw received in the bore, the bottom being first received in the opening during closure thereof; the improvement wherein the set screw is uploadable and received into the central bore of the fastener through the fastener bottom; said combination including an abutment structure interferingly prohibiting the set screw from advancing out of the top of the fastener; and the abutment structure extending from the fastener inwardly into the bore and being disposed near the fastener top.

* * * * *